United States Patent [19]

Kimmel et al.

[11] Patent Number: 4,752,447
[45] Date of Patent: Jun. 21, 1988

[54] OPTICAL FILTER WITH REVERSIBLE COLOR CHANGE

[75] Inventors: Heinrich Kimmel, Buckenhof; Bernhard Montag, Forchheim; Walter Gumbrecht, Erlangen, all of Fed. Rep. of Germany

[73] Assignee: Siemens Aktiengesellschaft, Munich, Fed. Rep. of Germany

[21] Appl. No.: 833,729

[22] Filed: Feb. 26, 1986

[30] Foreign Application Priority Data

| Feb. 26, 1985 | [DE] | Fed. Rep. of Germany | 3506686 |
| Feb. 26, 1985 | [DE] | Fed. Rep. of Germany | 3506676 |
| Feb. 26, 1985 | [DE] | Fed. Rep. of Germany | 3506684 |

[51] Int. Cl.$^4$ ............................................ G01N 21/78
[52] U.S. Cl. ........................................ 422/56; 436/169
[58] Field of Search ........................ 422/56, 57, 55; 436/169

[56] References Cited

U.S. PATENT DOCUMENTS

| 3,114,610 | 12/1963 | Gafford et al. | |
| 3,397,966 | 8/1968 | Plantz | 422/55 X |
| 3,455,656 | 7/1969 | Roberts et al. | |
| 3,754,867 | 8/1973 | Guenther | |
| 3,873,269 | 3/1975 | Kraffczyk et al. | 422/56 X |
| 3,920,402 | 11/1975 | Afanasiev et al. | |
| 4,115,067 | 9/1978 | Lyshkow | 422/56 |
| 4,248,597 | 2/1981 | McNeely | 422/56 X |
| 4,251,223 | 2/1981 | White | 422/56 X |
| 4,258,000 | 3/1981 | Obermayer | 422/56 X |
| 4,362,645 | 12/1982 | Hof et al. | 422/56 X |
| 4,398,183 | 8/1983 | Ando | 422/56 X |
| 4,407,960 | 10/1983 | Tratnyek | 422/56 X |
| 4,436,819 | 3/1984 | Manning | 422/56 X |
| 4,447,542 | 5/1984 | Gantzer | 422/56 X |
| 4,478,792 | 10/1984 | McConnaughey et al. | 422/56 |
| 4,485,665 | 12/1984 | Norman | 422/56 X |
| 4,567,019 | 1/1986 | Lawton | 422/57 |
| 4,587,100 | 5/1986 | Amano et al. | 422/56 |

*Primary Examiner*—Kathleen J. Prunner
*Attorney, Agent, or Firm*—Kenyon & Kenyon

[57] ABSTRACT

The present invention is directed to an optical filter that includes a mixture of at least one basic or acid color former or dye, preferably being a triphenyl methane system and at least one complementary acid or basic compound. The mixture reversibly changes color in response to a gas or vapor. The mixture may be embedded in a matrix substance and/or may be applied to a carrier. The color change may be measured photo-electrically.

11 Claims, 2 Drawing Sheets

OPTICAL FILTER WITH REVERSIBLE COLOR CHANGE

FIELD OF THE INVENTION

The present invention relates to optical filters that reversibly change color in response to certain gases or vapors, particularly, optical filters for the continuous measurement of the partial pressure of gases and vapors.

BACKGROUND OF THE INVENTION

The methods and substances used heretofore for the measurement of the partial pressure, i.e., concentration, of gases and vapors, for instance, test tube methods do not provide a continuously operating determination method for measuring a particular gas constituent.

Continuous measurement is possible with mass spectrophotometry. However, the determination capabilities and accuracies attainable with such expensive devices are often not necessary.

Known chemically sensitive sensors for the continuous measurement of the partial pressure of gases and vapors that operate with heated helices or metal oxide films can only be used at high temperatures and are only useful for measuring a few gases. Sensors which operate with solid electrolytes or with palladium gate field-effect transistors are useful only for the measurement of oxygen and hydrogen, respectively.

SUMMARY AND OBJECTS OF THE INVENTION

It is an object of this invention to provide optical filters which do not exhibit the above-described disadvantages and are suitable, due to their properties, for the continuous measurement of the partial pressures of a large number of gases and vapors at room temperatures.

The present invention provides optical filters which comprise a mixture of at least one basic or acid color former or dye and at least one complementary acid or basic compound. These mixtures undergo a reversible color change and/or extinction modification when exposed to certain gases or vapors. The mixture may be applied to an optically transparent carrier or may be embedded in a matrix substance which has different permeability and/or affinity for different gases. The mixture upon exposure to the gas or vapor constituent to be measured, possibly mixed with air, may exhibit a color change corresponding or proportional to the partial pressure of the vapor or gas to be measured.

DETAILED DESCRIPTION OF THE INVENTION

Optical filters according to the invention permit the measurement of the partial pressure or the concentration of gases and vapors at room or ambient temperatures in a simple manner. Since they also work reliably in the presence of carrier gas, especially air, the optical filters according to the invention can also be used for the monitoring of work stations or for monitoring within the scope of environmental protection. The reversible color change and/or extinction value change obtained upon exposure to a gas or vapor constitutent to be measured may be proportional to the concentration/partial pressure of the constitutent to be measured.

With an optical filter according to the invention the concentration of gases such as ammonia, as well as, vapors, for instance, solvent vapors such as acetone, alcohol, chloroform, ethyl acetate or the like may be determined. The reversible color change correlates with the concentration of the acting gas or vapor and the detection limits may be as low as about 10 ppm.

The transmitivity change which results is preferably measured photometrically with a detector means, such as, photo diode, phototransistor, photoresistor or photocell in combination with a light source, such as, a light emitting diode, incandescent lamp, discharge lamp, chemoluminescent device or photoluminescent device.

Suitable acid color formers are triphenyl-methane systems and a suitable basic color former is crystal violet lactone.

Suitable dyes include triphenyl methane dyes such as phthaleines, especially phenolphthalein or sulfone phthaleines, especially bromothymol blue.

Suitable complementary acid compounds include bisphenol-A, salicylic acid and o-nitrobenzoic acid.

Suitable complementary basic compounds include p-toluidine and p-chloroaniline.

Suitable substrate materials include ceramics, glasses and plastics, such as, polyacrylate and polytetrafluorethylene.

Suitable matrix substances, in which the mixture can be embedded include, polyethylene, polyvinyl chloride, silicones and collodium.

Optical filters according to the invention can be used to advantage in components, e.g., integrated circuits and analysis equipment due to their compatibility with photoelectrically readable elements.

Figure 1:
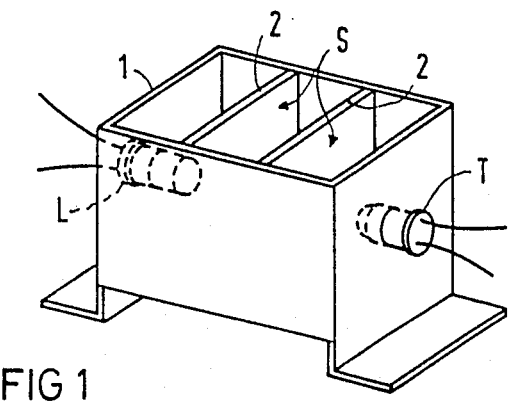
FIG. 1 is a perspective view of an instrument incorporating an optical filter constructed in accordance with the invention.

FIG. 1 illustrates enclosed frame 1 which is open at its top and bottom to assure a gas or vapor flow. A light-emitting diode L and a phototransistor T are mounted on two opposite surfaces of the frame 1. In the ray (light) path between diode L and transistor T there are two sheets 2 of polytetrafluorethylene (HOSTAPHAN ®) coated with a sensitive layer S comprising a mixture of at least one acid or basic color former or dye and a complementary acid or basic compound.

Figure 2:
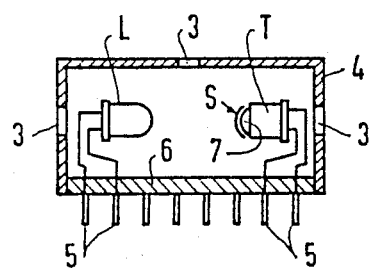
FIG. 2 is a sectional side view of FIG. 1.

FIG. 2 illustrates a dual in line (DIL) housing having several holes 3 that enable a gas or vapor to be measured to contact the sensitive layer S. In the interior of the DIL housing 4, a light-emitting diode L and a photo transistor T are mounted opposite one another. Electrical leads are attached to different connector pins 5 in a bottom plate 6. In this embodiment, the sensitive layer S is applied directly to the front lens 7 of the phototransistor T.

Figure 3:
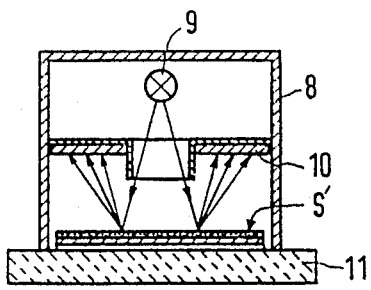
FIG. 3 illustrates an alternate embodiment of the invention employing a porous gas-permeable ceramic disc.

FIG. 3 illustrates a metal housing 8, with an incandescent lamp 9 (light source) which illuminates the sensitive layer S'. The light back-scattered or reflected from lamp 9 by layer S' is collected by an annular photosensitive layer 10. The sensitive layers S' are applied to a porous gas-permeable ceramic disc 11.

EXAMPLE I

An optical filter in accordance with this invention was prepared as follows: 30 mg crystal violet lactone, 70 mg bisphenol-A and 100 mg polyvinyl chloride were dissolved in 50 ml tetrahydrofurane and the solution was sprayed on a polyvinylacetate foil. The optical filter (see S of FIG. 1) was placed in a measuring setup according to FIG. 1 and subjected to different ethanol vapor pressures in air. The different ethanol vapor pressures were produced with ethanol/water mixtures of different concentrations. The different vapor pressures as measured with the chemically sensitive component of FIG. 1 are plotted in FIG. 4.

Figure 4:
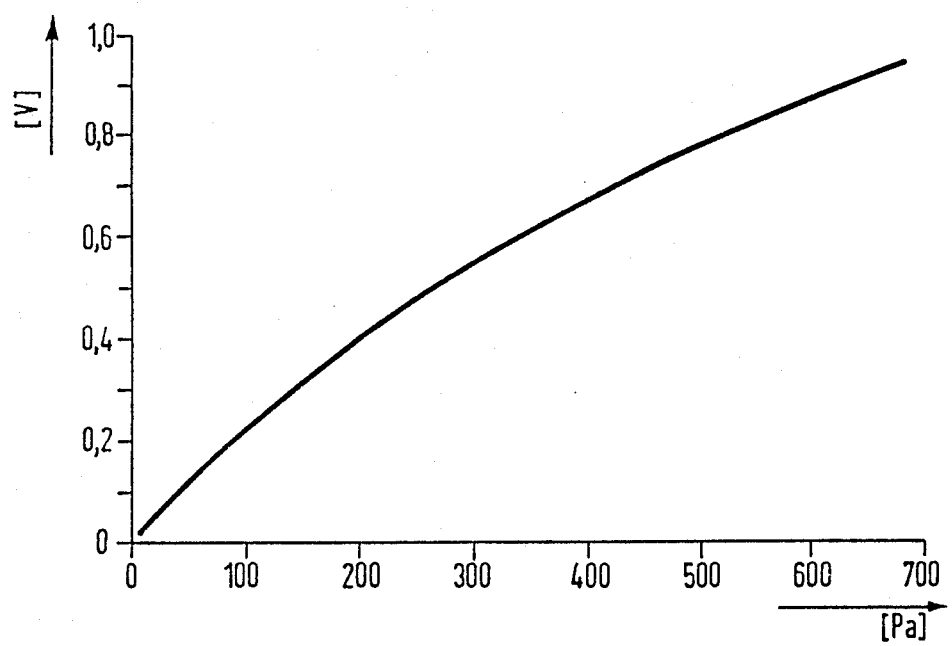
FIG. 4 is a plot illustrating the voltaic response of a photodetector including an optical filter constructed in accordance with the invention to ethanol vapor.

FIG. 4 is a plot with the ordinate representing the voltage caused by the photocurrent across a resistor, and the abscissa representing the ethanol vapor pressure in Pa in the measuring setup. It can be seen from FIG. 4 that the photocurrent increases with increasing ethanol vapor pressure. This increase is a result of the increasing transmissivity caused by the reversible color change in the sensitive layer.

EXAMPLE 2

Part of the solution above was sprayed directly on a photo transistor and inserted into the measuring arrangement according to FIG. 2.

What is claimed is:

1. An optical filter for the continuous measurement of the partial pressure of gases and vapors, comprising a mixture that undergoes a reversible color change or extinction modification when exposed to certain gases and is composed of at least one compound selected from the group consisting of a basic color former, and acid color former and a dye with at least one compound selected from the group consisting of a complementary acid and a complementary basic compound.

2. The optical filter according to claim 1, wherein the dye is a triphenyl-methane.

3. The optical filter according to claim 2, wherein the dye is crystal violet lactone.

4. The optical filter according to claim 3, wherein the complementary acid compound is bisphenol-A.

5. The optical filter according to claim 2, wherein the dye is selected from the group consisting of phthaleines and sulfone phthaleines.

6. The optical filter according to claim 1, wherein the complementary acid compound is a member of the group consisting of bisphenol-A and salicylic acid.

7. The optical filter according to claim 6, wherein the mixture is embedded in a matrix substance.

8. The optical filter according to claim 6, wherein the mixture is applied to a carrier.

9. The optical filter according to claim 1, wherein the basic complementary compound is selected form the group consisting of p-toluidine or p-chloroaniline.

10. The optical filter according to claim 9, wherein the mixture is embedded in a matrix substance.

11. The optical filter according to claim 9, wherein the mixture is applied to a carrier.

* * * * *